(12) United States Patent
Seetharam et al.

(10) Patent No.: US 6,183,723 B1
(45) Date of Patent: *Feb. 6, 2001

(54) TRANSCOBALAMIN MEDIATED TRANSPORT OF VITAMINS $B_{12}$ IN INTRINSIC FACTOR OR RECEPTOR DEFICIENT PATIENT

(75) Inventors: Bellur Seetharam, Brookfield, WI (US); Santanu Bose, San Francisco, CA (US)

(73) Assignee: MCW Research Foundation, Milwaukee, WI (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/009,995

(22) Filed: Jan. 21, 1998

(51) Int. Cl.$^7$ ............................. A61K 49/00; A61K 38/00
(52) U.S. Cl. ................................. 424/9.2; 424/9.1; 514/2
(58) Field of Search ........................... 424/9.2, 9.1; 514/2

(56) References Cited

PUBLICATIONS

Barshop et al., "Transcobalamin II deficiency presenting with methylmalonic aciduria and homocystinuria and abnormal absorption of cabalamin", American Journal of Medical Genetics, 1990, vol. 35, pp. 222–228.*

Pathare et al., "Synthesis of cobalamin–biotin conjugates that vary in the position of cabalamin coupling. Evaluation of cabalamin derivative binding to transcoabalamin II", Bioconjugate Chem. , 1996, vol. 7, No. 2, pp. 217–232.*

Li et al., Isolation and sequence analysis of various forms of human transcobalamin II, Biochimica et Buophysica Act, 1993, vol. 1172, pp. 21–30.*

S. Bose, et al., "Membrane Expression and Interactions of Human Transcobalamin II Receptor," *J. Biol. Chem.* 270 (14):8152–8157, 1995.

S. Bose, et al., "Regulation of Expression of Transcobalamin II Receptor in the Rat," *Biochem. J.* 310:923–929, 1995.

S. Bose, et al., "Dimerization of Transcobalamin II Receptor," *J. Biol. Chem.* 271(20):11718–11725, 1996.

S. Bose, et al., "In vitro and in vivo Inactivation of Transcobalamin II Receptor by its Antiserum," *J. Biol. Chem.* 271(8):4195–4200, 1996.

S. Bose, et al., "Bipolar Functional Expression of Transcobalamin II Receptor in Human Intestinal Epithelial Caco–2 Cells," *J. Biol. Chem.* 272(77):3538–3543, 1997.

B.A. Cooper and D.S. Rosenblatt, "Inherited Defects of Vitamin $B_{12}$ Metabolism," *Ann. Rev. Nutr.* 7:291–320, 1987.

N. Dan and D.F. Cutler, "Transcytosis and Processing of Intrinsic Factor–Cobalamin in Caco–2 Cells," *J. Biol. Chem.* 269(29):18849–18855, 1994.

K.S. Ramanujam, et al., "Expression of Cobalamin Transport Proteins and Cobalamin Transcytosis by Colon Adenocarcinoma Cells," *Am. Physiol. Soc.* pp. G416–G422, 1991.

K.S. Ramanujam, et al., "Leupeptin and Ammonium Chloride Inhibit Intrinsic Factor Mediated Transcytosis of [$^{57}$Co] Cobalamin across Polarized Renal Epithelial Cells," *Biochem. Biophys. Res. Comm.* 182(2):439–446, 1992.

M. Ramasamy, et al., "Cobalamin Release from Intrinsic Factor and Transfer to Transcobalamin II within the Rat Enterocyte," *Am. Physiol. Soc.*, pp. G791–G797, 1989.

B. Seetharam, "Gastrointestinal Absorption and Transport of Cobalamin (Vitamin $B_{12}$)," Physiology of the Gastrointestinal Tract, Third Edition, L.R. Johnson, Raven Press, New York, pp. 1997–2026, 1994.

* cited by examiner

*Primary Examiner*—Sandra E. Saucier
*Assistant Examiner*—Vera Afremova
(74) *Attorney, Agent, or Firm*—Quarles & Brady LLP

(57) ABSTRACT

A method for oral treatment of patients using different types of drugs that are not usually transported to circulation, if administered orally, is disclosed. Because the TC II-Cbl complex is stable to acid and proteolytic enzymes both outside and inside the intestinal absorptive cells, the method consists of oral administration of a drug bound to TC II-Cbl complex. In addition, the method can also be used for delivering Cbl to a large number of patients who do not absorb Cbl due to a variety of causes such as surgery of their stomach (ulcers) or of their terminal ileum (Crohn's disease).

1 Claim, 6 Drawing Sheets

TRANSCOBALAMIN MEDIATED TRANSPORT OF VITAMINS $B_{12}$ IN INTRINSIC FACTOR OR RECEPTOR DEFICIENT PATIENT

STATEMENT REGARDING FEDERALLY SPONSORED RESEARCH OR DEVELOPMENT

This invention was made with United States Government support awarded by Grant No. NIDDK-50052. The United States Government has certain rights in this invention.

CROSS-REFERENCE TO RELATED APPLICATION

Not applicable.

BACKGROUND

The plasma transport of Cobalamin (Cbl; Vitamin $B_{12}$) to all tissues/cells occurs bound to a plasma transporter, transcobalamin II (TC II), by receptor-mediated endocytosis [1] via transcobalamin II-receptor (TC II-R). Recent studies [2] have shown that TC II-R is expressed as a non-covalent homodimer of molecular mass of 124 kDa in all human [2], rat [3] and rabbit [4] tissue plasma membranes. The plasma membrane expression of TC II-R is important for the tissue/cellular uptake of Cbl since its functional inactivation in vivo by its circulatory antiserum causes intracellular deficiency of Cbl which in turn results in the development of Cbl deficiency of the animal as a whole [4]. Although TC II-R is expressed in the plasma membrane of all cells, its polarity of expression in epithelial cells is not known.

Recent immunoblot studies [3] have revealed that in the rat kidney, TC II-R protein is expressed in both the isolated apical and basolateral membranes with an enrichment in the basolateral membranes by about 8 fold. However, how TC II-Cbl internalized via the TC II-R from either the apical or basolateral surface is processed is not known. Recent TC II-$^{57}$[Co]Cbl uptake studies [4] using filter grown polarized Caco-2 cells have shown that $^{57}$[Co]Cbl taken up from the basolateral side in these cells was utilized as Cbl coenzymes suggesting that these cells derive Cbl essential for their use from the basolateral side.

Despite these studies, the details of intracellular sorting of Cbl and TC II by a polarized epithelial cell are poorly understood. The present studies were undertaken to address the issues related to polarized expression and function of TC II-R in human intestinal derived Caco-2 cells, a well established cell model used extensively to study nutrient transport and general intestinal epithelial cell biology [5, 6].

Needed in the art of cell biology is a method by which cell surface receptors, such as TCII-R, that bind to polypeptide ligands can be used to transport various drugs, including Cbl, across epithelial cell barriers, such as the one that exists in the intestine.

SUMMARY OF THE INVENTION

The present invention is a method of treating a patient with a therapeutic drug, preferably a drug that cannot normally be administered orally because it is inactivated prior to absorption or is not absorbed. In one embodiment a hydrophobic drug, preferably a synthetic organic molecule, is conjugated to a cobalamin molecule. The cobalamin drug conjugate is then bound to transcobalamin II and an effective amount is orally delivered to the patient.

The cobalamin/drug conjugate bound to transcobalamin II will be transcytosed from the intestinal lumen to circulation as an intact complex. The complex present in the circulation will be taken up by all cells and following internalization be targeted to lysosomes, wherein the complex will be degraded and the drug liberated.

In another form of the present invention, physiological amounts of cobalamin are orally delivered to vitamin $B_{12}$-deficient patients. An effective amount of the complex of transcobalamin II-cobalamin will be supplied and orally ingested by patients.

In another embodiment of the present invention, a drug is conjugated directly to a transcobalamin II molecule and an effective amount is orally delivered to the patient.

In another embodiment, the present invention is the transcobalamin II-cobalamin-therapeutic drug complex. In another embodiment, the present invention is the transcobalamin II-therapeutic drug complex. In another embodiment, the present invention is the transcobalamin II-cobalamin complex.

It is a feature of the present invention that one is able to orally deliver therapeutic drugs to the circulation of a patient. This feature is especially important when the drug selected is one that is destroyed by acid or proteases if it is administered orally.

It is another feature of the present invention that one is able to deliver a therapeutic drug across the gastrointestinal tract to the circulation of the patient through the mediation of the transcobalamin II receptor expressed in the gastrointestinal tract.

Other features, advantages and objects of the present invention will become apparent after review of the specification, claims and drawings.

DESCRIPTION OF THE INVENTION

In General

Figure 1:
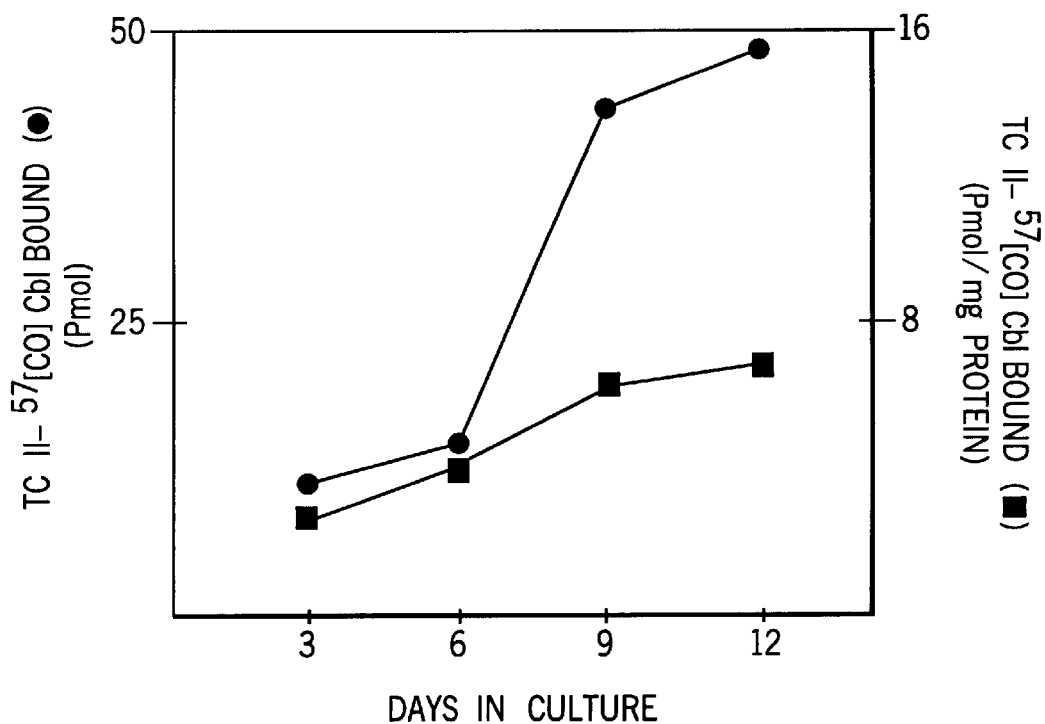
FIG. 1 is a graph demonstrating the transcobalamin II receptor activity during growth and differentiation of Caco-2 cells.

The Examples below disclose that transcobalamin II-receptor (TCII-R) total and specific activities in Caco-2 cells rose 5- and 2.7-fold, respectively during the differentiation of these cells from day 3–12 in culture. Filter-grown Caco-2 cells expressed TCII-R in both the apical and the basolateral membranes with an enrichment in the basolateral membranes by 6.8-fold. TCII-R expressed in both surface membranes was functional in the internalization of $^{57}$[Co]

Cbl bound to transcobalamin II (TC II). Following 5 hours of internalization from the apical side, all of the $^{57}$[Co]Cbl (~30 fmol) was transcytosed to the basolateral side still bound to TC II and lysosomotropic agents chloroquine or leupeptin had no effect on its transcytosis. On the other hand, following 5 hours of internalization from the basolateral side, all of the $^{57}$[Co]Cbl (~180 fmol) internalized was retained by the cells being transferred from TC II to other cellular proteins. Lysosomal inhibitors chloroquine or leupeptin inhibited (65–70%) the intracellular retention of $^{57}$[Co]Cbl and all of the Cbl radioactivity was now bound to TC II being distributed in the intracellular (35–45%, 55–65 fmol) compartments and the basolateral (55–65%, 120–125 fmol) medium. In the presence or absence of lysosomal inhibitors intact 43 kDa $^{125}$I-TC II was transcytosed from the apical to the basolateral side following the apical uptake of $^{125}$I-TC II-Cbl. In contrast, in the absence of lysosomal inhibitors, $^{125}$I-TC II was degraded inside the cell and the degraded (28 kDa) TC II was secreted back into the basolateral medium following the basolateral uptake of $^{125}$I-TC II-Cbl. In the presence of lysosomal inhibitors, labeled TC II accumulated both in the cell and in the basolateral medium. When $^{125}$I-TC II-Cbl was orally administered to rats, intact 43 kDa labeled TC II was detected in the portal blood 4 and 8 h later.

Based on these studies we suggest that a) Caco-2 cells process TC II-Cbl by a hitherto unrecognized non-lysosomal pathway in which both TC II and Cbl are transcytosed following apical endocytosis of TC II-Cbl via TCII-R, b) TCO II-Cbl endocytosed from the basolateral side in Caco-2 cells is processed via the lysosomal pathway in which TC II is degraded and the released Cbl is utilized and c) TCII-R expressed in the apical membranes of the rat intestinal mucosa is also functional in mediating endocytosis and eventual transcytosis, if the ligand, TC II-Cbl is presented to the intestinal lumen.

Drug Delivery Systems

The Examples below disclose that the plasma transport of cobalamin (Cbl; Vitamin $B_{12}$) is mediated by the plasma transporter, transcobalamin II (TC II). The circulatory Cbl bound to TC II is delivered to all cell/tissues by receptor-mediated endocytosis via Transcobalamin II-Receptor (TCII-R). The newly discovered non-lysosomal pathway of TC II-Cbl transcytosis from the apical (luminal) to the basolateral (circulation) side via TCII-R may be used as a mode of oral delivery of therapeutic drugs and the delivery of Cbl for the treatment of Cbl-deficient patients.

Thus, the method of the present invention begins with the conjugation of either a therapeutic drug, preferably a hydrophobic drug such as a synthetic organic molecule, to Cbl. Preferred methods of attaching the therapeutic drug to the Cbl molecule are described below. In one embodiment, the preferred drug can be conjugated to Cbl via biotin. Biotin is conjugated to either the propionamide or the acetamide side chains of the corrin ring of the Cbl Molecule. When conjugated to the e-side chain, the Cbl-biotin complex binds well to transcobalimin II. The initial biotin-Cbl complex can be prepared according to Pathre, et al. (Pathre, P. M., et al., "Synthesis of Cobalamin-Biotin conjugates that vary in the position of cobalamin coupling, Evaluation of cobalamin derivative binding to transcobalamin II," incorporated by reference).

In addition to conjugation of the side chains of the corrin ring, conjugation to the Cbl moiety can also be made to the ribose moiety, phosphate moiety, and to the benzimidazole moiety. The conjugating agent and the drug to be conjugated depend upon the type of Cbl group that is modified and the nature of the drug and may have to standardize for each drug. One of skill in the art would understand how to adapt the conjugation method to the particular Cbl group and drug to be coupled.

By "Cbl" or "cobalamin" we mean vitamin $B_{12}$. Vitamin $B_{12}$ is commercially available in its most stable form as cyanocobalamin with Sigma Chemical (St. Louis, Mo.).

One may most easily obtain transcobalamin II in the following manner: Transcobalamin II cDNA is available in the laboratories of Drs. Seetharam (Medical College of Wisconsin) and Rothenberg (VA-Hospital, New York) (see Li, N., et al., *Biochim. Biophys. Acta.* 1172:21–30, 1993 and Platica, O., et al., *J. Biol. Chem.* 266:7860–7863, 1991 for description of cloning strategy). TC II cDNA can be expressed in Baculovirus system to make a large amount of functionally active TC II protein (see Quadros, E. V., et al., *Blood* 81:1239–1245, 1993). One of skill in the art would be able to reproduce the TC II cDNA.

In a preferred embodiment, these complexes are created by genetic engineering. In this method, a DNA sequence encoding TC II and the peptide drug may be expressed as one chimeric molecule. For example, it is possible to generate a chimeric construct using the full-length TC II cDNA and the cDNA for a peptide drug (e.g., insulin). The chimeric construct can then be expressed to produce a protein combination to TC II-peptide drug. Following synthesis, the chimeric protein should be tested for both TC II activity and the drug activity. Cobalamin can then be allowed to bind to this chimeric protein and used for oral therapy.

In another embodiment, one may wish to deliver cobalamin to a patient's circulatory system. In this embodiment of the invention, one prepares a cobalamin-transcobalamin II complex, preferably by incubating TC II with Cbl. The unbound Cbl can be separated from the TC II-bound Cbl by adding albumin-coated charcoal. Following centrifugation, the free Cbl is always found in the charcoal pellet and the TC II-bound Cbl is present in the supernatant, which is then carefully taken out with a Pasteur pipette (see Gottlieb, C., et al., *Blood* 25:875–884, 1965).

An effective amount of the transcobalamin II-Cbl-drug or transcobalamin II-Cbl complex is then orally ingested by the patient. As described below, the non-lysosomal pathway of TC II-Cbl allows the drug or Cbl to be delivered into the circulatory system.

The present invention is also a therapeutic dose of the transcobalamin II-cobalamin-drug, transcobalamin II-drug or transcobalamin II-cobalamin complex combined with pharmaceutical carriers.

This particular pathway can be used for oral treatment of various disorders including:

1. Cbl deficiency—Patients with inherited (absorption deficiency due to the absence of functional Cbl absorption proteins including IF, TC II and IFCR) or acquired (surgery) causes of Cbl deficiency can be treated orally with TC II-Cbl. Because TCII-R is expressed in the entire region of the gut (S. Bose, et al., *Biochem. J.* 310:923–929, 1995), the orally administered TC II-Cbl complex internalized from the luminal side will be transcytosed as an intact TC II-Cbl complex to the circulation (basolateral side) via a non-lysosomal pathway. The circulatory TC II-Cbl complex, once endocytosed by TCII-R expressed in the cell surface of all cells and tissue, will be targeted to lysosomes. In the lysosomes, TC II will be degraded and the free Cbl will be used by the cells for cellular metabolic reactions (S. Bose, et al., supra, 1997). This type of oral Cbl therapy will be highly beneficial for Cbl deficient patients, who at the present time are being regularly treated with high dosage of intramuscularly injected Cbl.

2. Other disorders—This novel pathway can also be exploited to orally deliver therapeutic drugs to patients suffering from various disorders. In one embodiment, a hydrophobic drug, such as a synthetic organic molecule, can be conjugated to the Cbl molecule. The Cbl-drug conjugate bound to TC II will be transcytosed to the circulation as an intact complex when it is presented orally. From the circulation, the complex (TC II-Cbl-drug) once endocytosed by all cells via TCII-R, will be targeted to lysosomes. In the lysosomes, following degradation of TC II, Cbl will be released from the drug intracellularly. The liberated drug can then act on its intracellular target molecules, once it is transported out of the lysosomes.

In another embodiment, a drug can be conjugated directly to the TC II molecule.

In order to successfully use this pathway for oral delivery of drugs to their intracellular targets, the following three factors have to be taken into consideration:

a. Affinity of drug conjugated Cbl for TC II—Recently different organic molecules including biotin (P. Pathare, et al., Bioconjugate. Chem. 7:217–232, 1996) and arylstannyl (D. Wilbur, et al., Bioconjugate. Chem. 7:461–474, 1996) were successfully conjugated to the different functional groups of the Cbl molecule using a spacer arm. The results from these studies have also confirmed that conjugation at 5'-OH ribose moiety, cobalt metal center and in the e'-propionamide side chain of Cbl had little effect on binding of modified Cbl to TC II (P. Pathare, et al., supra, 1996; D. Wilbur, et al., supra, 1996; R. Bonnett, "Reactions of the Corrin Macrocycle," B12: Vol 1-Chemistry, pp. 201–243, Wiley, New York, 1982). Accordingly, the drug of interest is preferably conjugated to these side groups of Cbl, so that it does not alter the affinity of modified Cbl for TC II.

b. Binding affinity of TC II-Cbl-drug complex for TCII-R and the rate of its internalization—Bio-distribution studies (D. Wilbur, et al., supra, 1996) in mice using TC II complexed to radiolabelled Cbl that has been conjugated to different organic molecules at the sites mentioned above have demonstrated that there were no chances in the distribution of modified Cbl radioactivity in different organs, compared to control experiments. These studies have clearly shown that conjugated Cbl bound to TC II can be efficiently endocytosed by TCII-R expressed in all cells/tissues.

c. Intracellular diconjugation of the complex—Earlier studies have shown that TC II-Cbl complex is targeted to lysosomes following its internalization by TCII-R. In the lysosomes, TC II is degraded and free Cbl is utilized by the cells. Because the rate of internalization of modified TC II-Cbl complex (TC II-Cbl-organic molecule conjugate) was shown not to be effected (discussed earlier), the TC II-Cbl-drug complex will also be targeted to lysosomes. In the acidic environment of the lysosomes and in the presence of proteolytic enzymes, the bond between the Cbl and the conjugated molecule will be cleaved. Earlier studies have demonstrated the intracellular cleavage of esterified conjugated molecule from Cbl by intracellular enzymes, including esterases (E. Quadros, et al., "Vitamin B12, pp. 1045–1054, Walter d Gruytr & Co., New York, 1979; E. Quadros and D. Jacobsen, *Biochim. Biophys. Acta* 1244:395–403, 1995).

EXAMPLES

In General

The results of this study show that TCII-R is asymmetrically expressed in the ratio of 1:7 and 1:6.8 in the apical and the basolateral membranes of human intestinal mucosa and intestinal derived Caco-2 cells, respectively. Furthermore, when TC II-Cbl is presented on the apical side of Caco-2 cells or to the intestinal lumen of rats, TC II is transcytosed across the epithelial cell by a non-lysosomal pathway. In addition, these studies also demonstrate that when presented on the basolateral side, TC II is processed via the lysosomal pathway, resulting in the degradation of TC II and the utilization of intracellularly released Cbl as coenzymes.

Materials and Methods

Materials-The following chemicals and reagents were obtained as indicated: [$^{57}$Co] Cyanocobalamin (specific activity, 15 $\mu$Ci/$\mu$g) and carrier free Na$^{125}$I (Amersham Corp.); sulfosuccinimidobiotin (S-NHS biotin)(Pierce); Millicell HA culture plate inserts (Millipore); Cellulose nitrate membranes (Schleicher and Schuell); Rabbit serum (Life Technologies Inc.); Human Serum (Blood Center of Southeastern Wisconsin) and Chloroquine and leupeptin (Sigma Chemicals); Dulbecco's Modified Eagle's medium (DMEM) and trypsin-EDTA (Gibco-BRL). Human intestinal mucosa was obtained during autopsy of an unidentified donor from Frodetert Memorial Lutheran Hospital, Milwaukee, Wis.

Pure human TC II was a gift from late Charles A. Hall (Nutrition Assessment Laboratories, VA Hospital, Albany, N.Y.). Goat antiserum to rabbit TC II was a gift from Dr. Robert H. Allen (University of Colorado Health Science Center, Denver, Colo.)

Cell culture-Caco-2 cells (passages 76–80) were grown in DMEM (25 mM glucose) supplemented with 20% heat-inactivated fetal bovine serum, 4 mM glutamine, 100 U/ml penicillin, and 100 $\mu$g/ml streptomycin in a humidified atmosphere containing 5% $CO_2$. Confluent monolayers were subcultured every 7 days by treatment with 0.05% trypsin-EDTA in phosphate-buffered saline. In some experiments the cells were plated at a density of $2 \times 10^6$ cells on plastic (T-75 cm$^2$ flasks) and were harvested 3–12 days after plating. For the ligand uptake studies cells were grown as epithelial layers by high density seeding ($1.5 \times 10^6$ cells/filter) onto nitrocellulose membrane filter inserts (Millicell-HA, 30 mm diameter, 0.45 $\mu$M pore size). The formation and integrity of monolayers were assessed by the development of significant transepithelial resistance of 250–300 ohms/cm$^2$ over the resistance of filter alone. All resistance readings were measured with Millicell-ERS Voltohmeter (Millipore). Antiserum to human TCII-R [2] and human TC II [7] was prepared as described earlier. TC II free of transcobalamins I and III was partially purified from both rabbit and human serum according to Lindemanns, et al. [8] and used as ligand for uptake studies. Human TC II (5 $\mu$g) and streptavidin (50 $\mu$g) were each iodinated with 0.5 mCi of Na$^{125}$I and IODO-GEN, as recommended by the manufacturer (Pierce). The specific activity of iodinated TC II was 70–75 $\mu$Ci/$\mu$g.

TC II-$^{57}$[Co]Cbl binding and uptake studies in filter grown Caco-2 cells- Post-confluent Caco-2 cells grown on culture inserts were incubated with human or rabbit TC II-[$^{57}$Co] Cbl (500 fmol) at 5° C. for 30 minutes either apically or basolaterally to determine the surface binding. After 30 minutes, the medium was removed, cells washed in cold medium, and the amount of TC II-$^{57}$[Co]Cbl bound to the surface membrane was determined by counting the radioactivity in scraped cells. The TCII-R specific ligand binding was then calculated by subtracting the amount of ligand bound to the cell surfaces in the presence of TCII-R antiserum (5–20 µl) or that bound when the ligand was incubated at 5° C. in the presence of pH5/EDTA buffer. In general, the non-specific binding was less than 5% of the total ligand bound. Intracellular $^{57}$[Co]Cbl was determined by allowing the surface bound ligand to internalize for 1 h at 37° C. At the end of 1 hour, the cells were scraped and counted for $^{57}$[Co]Cbl. In a separate set of filters, the surface bound ligand from both surface membranes was incubated for 5 hours at 37° C. to measure the amount of [$^{57}$Co]Cbl transported across the apical and the basolateral membranes. In some experiments prior to the addition of the ligand the cells were incubated with either chloroquine (1 mg/ml) or leupeptin (1 mg/ml) added to both the apical and basolateral medium for 1 hour. The lysosomotropic agents were also present throughout the 5 hours period of incubation. During the apical ligand uptake studies, the basolateral surface was preincubated for 1 hour at 4° C. with TCII-R antiserum (20 µl), washed with antiserum free medium and then warmed to 37° C. and the ligand was presented apically. Such a treatment was essential to ensure that TC II-$^{57}$[Co]Cbl that was transcytosed from the apical to the basolateral side did not re-enter the cell via basolateral TCII-R.

The radioactive Cbl present in the basolateral medium following internalization from the apical domain or from the basolateral domain of cells incubated with lysosomotropic agents was counted in a gamma counter and then immunoprecipitated with polyclonal antiserum to either rabbit or human TC II. Briefly, 2 ml of the basolateral medium containing 23,000–150,000 dpm was treated with TC II antiserum (5–10 µl) and protein A-Sepharose (25–100 µl of 1:1 suspension in phosphate-buffered saline) and incubated for 18 hours at 5° C. The reaction mixture was centrifuged and radioactive Cbl immunoprecipitated was counted in a gamma counter. Intracellular $^{57}$[Co]Cbl was determined by the immunoprecipitation of Triton X-100 (1%) extract of the cellular homogenates (500 µl of Tris-HCl buffer pH 7.4 containing 140 mM NaCl and 0.1 mM PMSF) with antisera (5 µl) to either human or rabbit TC II as above.

When $^{125}$I-TC II-Cbl was used as a ligand to study sorting of TC II from both surface domains, the filter grown cells were incubated at 5° C. for 30 minutes with 350,000 dpm of $^{125}$I-TC II-Cbl (Specific activity 680 dpm/fmol) either oil the apical or the basolateral side. The medium was removed, cells washed in cold medium, and then the surface bound ligand was allowed to internalize for 1 hour at 37° C. to measure the intracellular labeled TC II. Intracellular levels of $^{125}$I-TC II was determined as follows: The cells were washed with pH 5.0. EDTA buffer to remove any surface radioactivity that may be still bound to the cell surfaces. Less than 1% of the radioactivity was removed from either surfaces by this treatment. The cells were then washed with Tris-HCl buffer pH 7.4 containing 0.1 mM PMSF, scraped from filters and homogenized in the same buffer (500 µl) and the radioactivity was counted in a gamma counter. The cell pellet collected by centrifugation containing 15,000–100,000 dpm was then treated with non-reducing SDS-PAGE buffer. The liberated radioactivity (10,000–65,000 dpm) was subjected to SDS-PAGE (10%). In a separate set of filters, the surface bound $^{125}$I-TC II-Cbl was incubated for 5 hours at 37° C. The $^{125}$I-radioactivity present in the basolateral medium (2 ml) was counted in a gamma counter. The medium was then treated with trichloroacetic acid (10%) and the precipitated radioactivity (>90%) was washed with acetone to remove TCA. The washed pellet was then treated with non-reducing SDS-PAGE buffer and the liberated radioactivity was subjected to SDS-PAGE (10%).

SDS-PAGE analysis and immunoblotting—Isolated total, basolateral and apical membranes from human ileal mucosa were subjected to non-reducing SDS-PAGE (7.5%) according to Laemmli [9]. Separated proteins were electroblotted for 90 minutes to detect optimal levels of TCII-R dimer onto Nitrocellulose membranes and probed with TCII-R antiserum as described before [2, 10].

Cell surface biotinylation-Biotinylation of Caco-2 cell surface proteins was carried out by adding S-NHS-biotin (0.5 mg/ml) to the apical and basolateral compartments of filter grown monolayers (12 day growth) and was performed a total of three times for 30 minutes each at 4° C. in PBS containing 0.1 mM CaCl$_2$, 1.0 mM MgCl$_2$. The cells were then washed 6 times in PBS containing 0.1 mM CaCl$_2$, MgCl$_2$ and 50 mM glycine (5 minutes each) at 4° C. The cells were then harvested and extracted with PBS containing Triton X-100 (1%). The extract was immunoprecipitated with TCII-R antiserum (25 µl) and protein A-Sepharose (100 µl of 1:1 suspension in PBS). The washed immunepellet was subjected to non-reducing SDS-PAGE (7.5%) and the bands were transferred to Nitrocellulose membranes and probed with $^{125}$I-streptavidin (3×10$^7$ dpm/blot) and the bands were visualized by autoradiography as described above.

In Vivo transport of TC II in rat- Six male adult rats (150 g) were orally administered with $^{125}$I-TCII-Cbl (1×10$^6$ dpm of TC II, Cbl bound 1.5 pmol) using feeding tube as described earlier [11]. Four and 8 hours following the oral administration of the ligand, the rats were anesthetized, and blood was drawn from the portal vein between the intestine and the liver. Serum prepared from the whole blood drawn after 4 hours and 8 hours of oral administration contained 50–75×10$^3$ and 150–200×10$^3$ dpm/ml, respectively. One-fourth the radioactivity in each of the samples was subjected to non-reducing SDS-PAGE (10%). The gels were dried and the radioactive bands were visualized by autoradiography at –70° C. using Kodak XAR-5 film. Similar results were obtained on SDS-PAGE using radioactive serum from each of the six rats used in the study.

Other methods-Protein in all samples was determined according to Bradford [12]. TCII-R activity in Caco-2 cell homogenate and isolated human intestinal membranes were determined using Triton X-100 (1%) extracts of these fractions by the DEAE-Sephadex method of Seligman and Allen [13]. Total membranes from human ileal mucosa was obtained by centrifuging at 100,000× g a 10% homogenate of the mucosa prepared in 10 mM Potassium-phosphate buffer pH 7.0 containing 0.25 M sucrose and 5 mM EDTA. The apical membranes from the human ileum was prepared by the Ca$^{++}$ aggregation method of Kessler, et al. [14]. The apical membrane was enriched for the apical markers, intrinsic factor-cobalamin receptor (10-fold) and alkaline phosphatase (17-fold) and contained <1% of the basolateral membrane marker, Na$^+$/K$^+$ ATPase and other intracellular membrane components, NADPH-cytochrome c reductase and β-glucuronidase. The mucosal basolateral membrane was isolated by the method of Molitoris and Simon [15]. TCII-R activity was enriched 8-fold and the basolateral marker Na$^+$/K$^+$ was enriched about 15-fold. The activity of apical markers alkaline phosphatase and IFCR, were present in amounts less than 1%.

Results

Transcobalamin II-receptor Expression in Caco-2 Cells

In order to examine TCII-R activity in Caco-2 cells as a function of cellular proliferation and differentiation, its activity was determined in cells that were grown on plastic for 3–12 days [FIG. 1]. FIG. 1 shows transcobalamin II-receptor activity during the growth and differentiation of Caco-2 cells. Caco-2 cells grown on plastic for 3–12 days were harvested and homogenized in 10 mM Tris-HCl buffer pH 7.4 containing 140 mM NaCl and 0.1 mM PMSF. The homogenate was extracted with Triton X-100 (1%) and the supernatant was assayed for the binding of TC II-$^{57}$[Co]Cbl (2 pmol) according Seligman and Allen [13]. Each data point is the average of duplicate assays from two separate batch of cells grown for 3–12 days. In general the results varied by less than 5%.

Total TCII-R activity in the cellular homogenate rose by about 5-fold (from 11–49 pmol) from day 3 to day 12 in culture. When the activity was expressed/mg of cellular protein, it rose by nearly 2.7-fold (2.7–7.2 pmol/mg protein). These results demonstrated that TCII-R activity in these cells is regulated during their differentiation and that the highest level of its expression occurred after reaching confluency. In all further studies, post-confluent cells grown for 12 days were used.

Bipolar expression of TCII-R in human intestinal mucosa and filter grown Caco-2 cells-Immunoblotting studies [3] using isolated apical and basolateral membranes from rat kidney and ligand binding studies using isolated rabbit intestinal surface membranes [4] have indicated that TCII-R protein and activity is enriched on the basolateral domain by nearly 8–10-fold. In order to confirm the bipolar asymmetric TCII-R protein and activity distribution between the apical and the basolateral surfaces in human intestine and in human intestinal derived Caco-2 cells, its activity and protein distribution was determined by using isolated human intestinal surface membranes and filter grown polarized Caco-2 cells. TCII-R activity in the human apical membranes was 1.4 pmol/mg protein which was about 7-fold less than 11 pmol/mg protein of receptor activity noted in the basolateral membranes.

Figure 2:
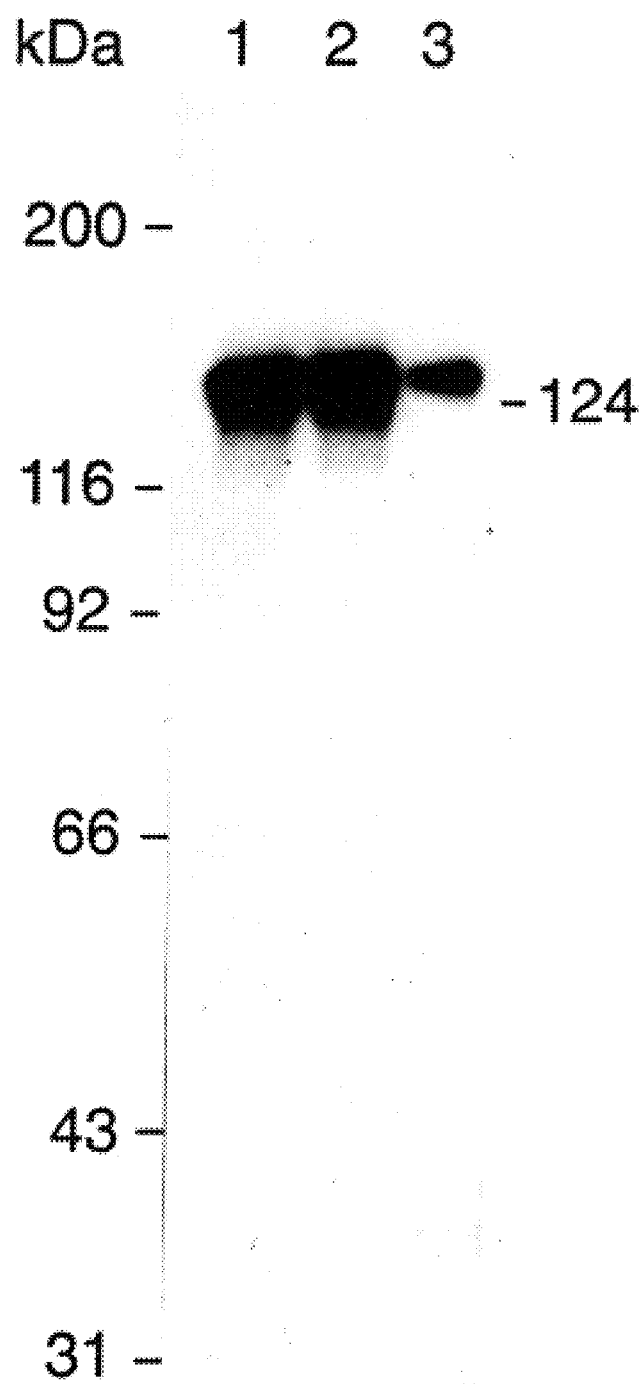
FIG. 2 is an immunoblot analysis of total, apical and basolateral membranes from the human intestinal mucosa.

Immunoblot analysis of isolated human intestinal total, apical and basolateral membranes [FIG. 2] and domain specific biotinylation of filter grown Caco-2 cells was carried out [FIG. 3]. FIG. 2 shows immunoblot analysis of total, apical and basolateral membranes from human intestinal mucosa. Total (lane 1), Basolateral (lane 2) and apical (lane 3) membranes (50 µg protein) were separated on non-reducing SDS-PAGE (7.5%) and the separated proteins were electroblotted onto Nitrocellulose for 90 minutes and probed with antiserum to human placental TCII-R and $^{125}$I-protein A. The bands were visualized by autoradiography.

Figure 3B:
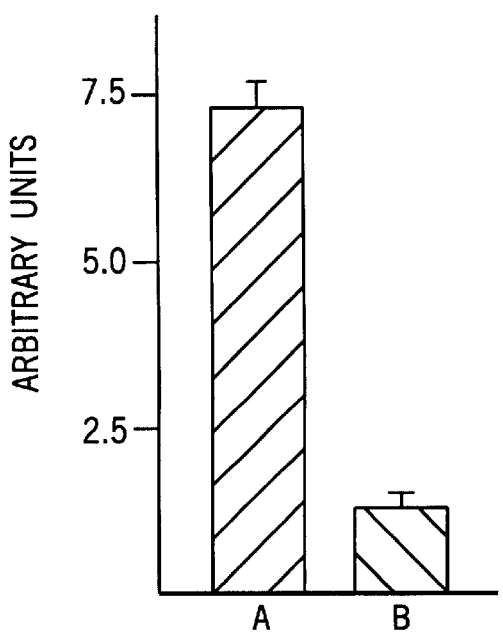
FIG. 3B is a bar graph quantifying the bands from the gel in FIG. 3A.
Figure 3A:
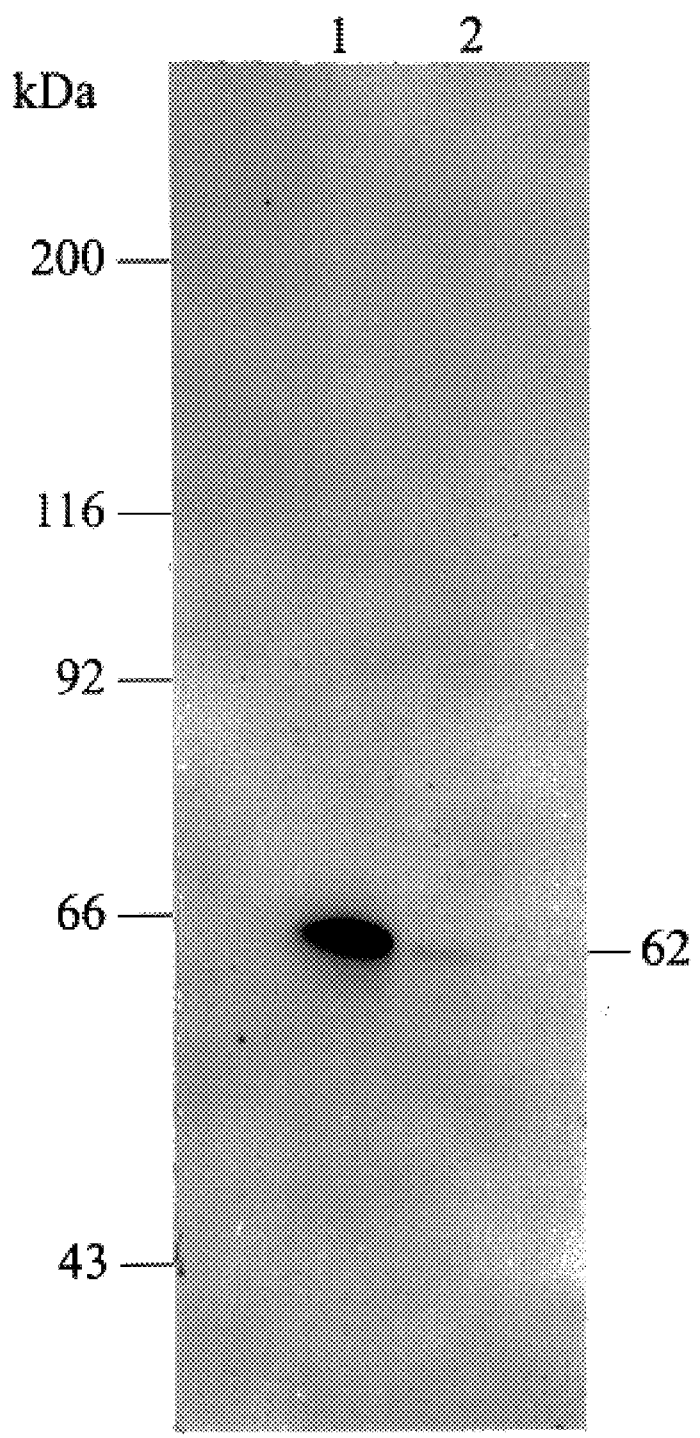
FIG. 3A is a photograph of a gel panel showing immunoprecipitated biotinylated TCIIR expressed in the apical and basolateral domains of Caco-2 cells separated on a non-reducing SDS-PAGE.

FIG. 3 demonstrates domain specific biotinylation of Caco-2 cells. Post-confluent Caco-2 cells grown on Millipore culture inserts were biotinylated with S-NHS-biotin as described in the methods. FIG. 3A shows detection of immunoprecipitated biotinylated TCII-R separated on non-reducing SDS-PAGE (7.5%) using $^{125}$I-streptavidin in basolateral (lane 1) and apical (lane 2) membranes. FIG. 3B shows the bands shown in FIG. 3A were quantified from gels using biotinylated membranes from three separate filters. "A" indicates basolateral and "B" indicates apical.

Quantitation of these blots [FIG. 2] revealed that the 124 kDa dimer form of TCII-R was enriched by 8-fold in the total [lane 1] and 7-fold in the basolateral membranes [lane 2] relative to its level of expression in the apical membrane [lane 3]. In the filter grown Caco-2 cells, domain specific biotinylation [FIG. 3, left panel] revealed TCII-R monomer of molecular mass of 62 kDa in both the basolateral [lane 1] and the apical [lane 2] cell surfaces. When the bands were quantitated [FIG. 3, right panel] for the image density, the receptor was enriched in the basolateral side [A] by nearly 6.8-fold relative to the apical side [B]. TC II-$^{57}$[Co]Cbl binding to these surface membranes revealed that receptor specific binding to the apical and basolateral membranes was 30 and 180 f mol/filter, respectively (Table I).

The absence of 124 kDa TCII-R dimer following domain specific biotinylation of filter grown Caco-2 cells is due to Triton X-100 extraction of the cells prior to treatment with TCII-R antiserum. Previously [2] we have shown that treatment of native membranes with Triton X-100 results in the total conversion of TCII-R dimer of molecular mass of 124 kDa into the monomer of molecular mass of 62 kDa. With the human intestinal membranes, immunoblotting [FIG. 2] did reveal very faint 62 kDa TCII-R monomers in the total [lane 1] and the basolateral membranes [lane 2].

Previously we have shown that TCII-R monomer levels are only 10% of the TCII-R dimer levels in any given tissue [3] and that the monomers are lost during 90 minutes electroblotting [10]. These studies have shown that apical expression of TCII-R activity/protein is a property of not only intact intestinal mucosa but also of cultured intestinal derived Caco-2 cells. In order to examine whether TCII-R expressed in both surface domains is functional in mediating endocytosis, we used filter grown Caco-2 cells to study binding and uptake of the ligand. Cellular sorting of $^{57}$[Co] Cbl bound to TC II—Filter grown cells were presented with the ligand, human TC II-$^{57}$[Co]Cbl on either the apical or basolateral cell surfaces. The ligand binding to cell surfaces at 5° C. revealed a basolateral binding of ~180 fmol/filter which was nearly 6-fold higher than the binding of ~30 fmol/filter noted on the apical side [Table I]. The specificity of ligand binding was confirmed when pre-incubation of cells with TCII-R antiserum on either side completely abolished ligand binding (data not shown). When the cells were warmed to 37° C. to allow for internalization of the ligand, within 60 minutes all the labeled Cbl had left both the apical and basolateral cell surfaces and 100% of $^{57}$[Co]Cbl was found inside the cell [Table I]. However, 5 hours following internalization, nearly 100% of Cbl internalized from the basolateral side was still present inside the cell while, greater than 95% of Cbl internalized from the apical side had exited the cell and was found transcytosed to the basolateral medium.

When the cells were pre-incubated with lysosomotropic agents, either chloroquine or leupeptin, the amount of $^{57}$[Co] Cbl that was transcytosed to the basolateral side following apical internalization of TC II-$^{57}$[Co]Cbl was not inhibited. In contrast, lysosomotropic agents inhibited the intracellular $^{57}$[Co]Cbl levels by nearly 65–70% following its basolateral entry and the inhibition was accompanied by increased $^{57}$[Co]Cbl levels in the basolateral medium. Both in the absence or in the presence of lysosomotropic inhibitors, basolaterally internalized Cbl was never transcytosed to the apical side [Table I]. These results suggested that apically internalized $^{57}$[Co]Cbl bound to TC II was transcytosed by a non-lysosomal pathway while, the basolaterally internalized $^{57}$[Co]Cbl was retained in the cell and that the lysosomotropic agents, chloroquine and leupeptin inhibited the cellular retention of $^{57}$[Co]Cbl. Immunoprecipitation of basolateral $^{57}$[Co] Cbl with antiserum to human TC II revealed (Table II) that all the Cbl radioactivity (~28 fmol) present in the basolateral medium following apical internalization of human TC II-$^{57}$[Co]Cbl in the presence and absence of lysosomal inhibitors was immunoprecipitated. In contrast, >than 90% of intracellular $^{57}$[Co]Cbl (~172–180 fmol) following internalization of TC II-$^{57}$[Co]Cbl from the basolateral side could not be immunoprecipitated with antiserum to human TC II when the cells were incubated in the absence of lysosomal inhibitors [Table II]. However, in the presence of lysosomal inhibitors, $^{57}$[Co]Cbl that was in the cell (55–65 fmol) and in the basolateral medium (120–124 fmol) was completely precipitated with human TC II antiserum [Table II].

Although the apically presented $^{57}$[Co]Cbl was completely transcytosed and was bound to TC II, it is not known whether the source of basolateral TC II is the internalizing exogenous TC II, or the endogenous Caco-2 cell TC II to which Cbl is transferred prior to transcytosis and following degradation of the exogenous internalizing TC II. To address this issue the following experiments were carried out. Our initial transcytosis studies using $^{57}$[Co]Cbl bound to rabbit TC II revealed that all of labeled Cbl in the basolateral medium could be precipitated with antiserum to rabbit TC II but not with antiserum to human TC II (data not shown). Native TC II complexed with $^{57}$[Co] Cbl from these two species can only be precipitated with their respective antiserum but not with antiserum raised to the other species [16]. Thus, this observation suggested that the source of TC II in the basolateral medium following apical internalization of TC II-Cbl is the exogenous TC II. In order to prove this directly, further transcytosis studies were carried out using $^{125}$I-TC II-Cbl.

TC II is Processed by Both Lysosomal and Non-lysosomal Pathways in Caco-2 Cells

Figure 4:
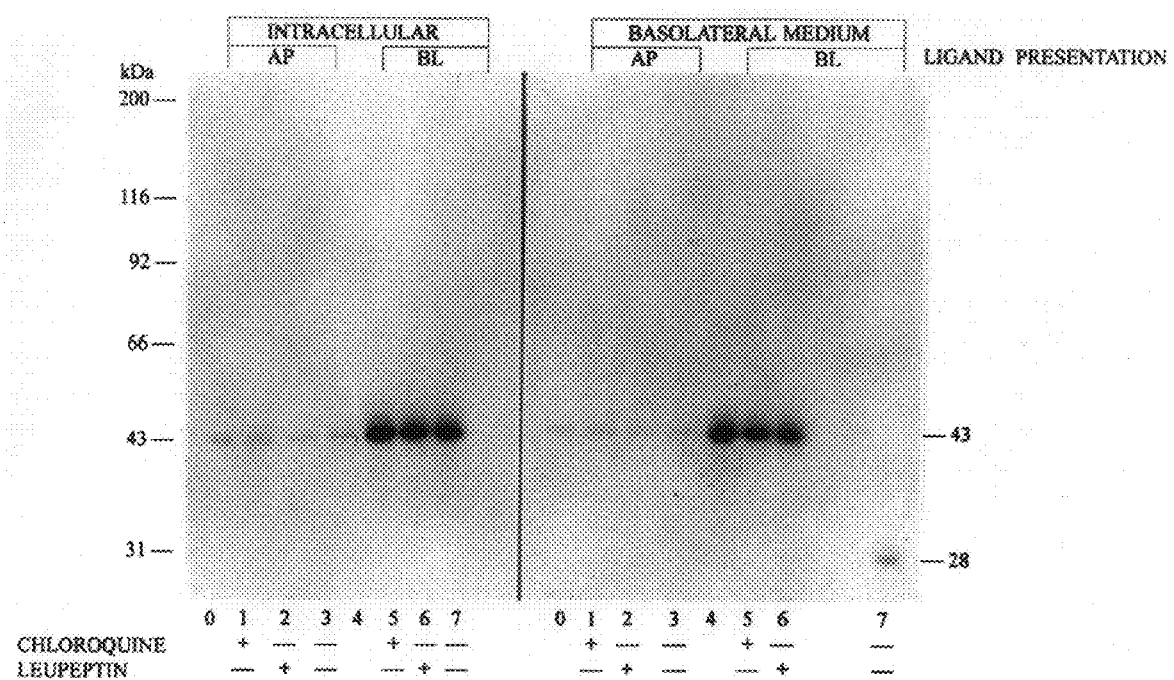
FIG. 4 is a photograph of SDS-PAGE analysis of intracellular and basolateral $^{125}$I-TC II-Cbl following internalization from the apical and basolateral sides of filter-grown Caco-2 cells.

FIG. 4 demonstrates SDS-PAGE analysis of intracellular and basolateral $^{125}$I-TC II-Cbl following internalization from the apical and basolateral sides of filter grown Caco-2 cells. FIG. 4A shows intracellular $^{125}$I-radioactivity following 1 hour internalization (37° C.) from the apical (lanes 1–3) and the basolateral (lanes 5–7) sides. Prior to the presentation of the ligand on either side the cells were preincubated with chloroquine (1 mg/ml, lanes 1 and 5) or leupeptin (1 mg/ml, lanes 2 and 6) or nothing (lanes, 3 and 7). Bands shown in lanes 0 and lanes 4 represent 10,000 dpm and 65,000 dpm of unincubated $^{125}$I-TC II-Cbl. FIG. 4B demonstrates basolateral medium $^{125}$I-radioactivity following internalization (5 hours at 37° C.) from the apical (lanes 1–3) and basolateral (lanes 5–7) sides. Other details are exactly as shown for the lanes in FIG. 4A.

When $^{125}$I-TC II-Cbl was presented on the apical side [FIG. 4, left panel], intact TC II could be detected inside the cell within 1 hour, both in the absence [lane 3] and the presence of lysosomotropic inhibitors, chloroquine [lane 1] or leupeptin [lane 2]. When the ligand was presented basolaterally, within 1 hour, no labeled TC II could be detected in the cell [lane 7] in the absence of lysosomotropic agents. However, intact TC II could be detected in the cells when the cells were incubated with either chloroquine [lane 5] or leupeptin [lane 6]. Following 5 hours of internalization, intact labeled TC II could be seen transcytosed to the basolateral medium both in the absence [FIG. 4, right panel, lane 3] or the presence of chloroquine [lane 1] or leupeptin [lane 2] when $^{125}$I-TC II-Cbl was internalized from the apical side. In contrast, when the ligand was presented to the basolateral side, intact TC II could be visualized in the basolateral medium only when the cells were exposed to chloroquine [lane 5] or leupeptin [lane 6]. In the absence of treatment of cells with lysosomotropic agents, the basolateral media contained degraded TC II of molecular mass of 28 kDa [lane 7], 15 kDa smaller than the native labeled TC II of molecular mass of 43 kDa [lane 0]. The bands shown in the left panel (lanes 0 and 4) and the right panel (lanes 0 and 4) represent unincubated $^{125}$I-TC II run on the same gels to match the intensities of $^{125}$I-TC II present in the cells (left panel) or in the basolateral medium (right panel). These results indicated that Caco-2 cells internalize TC II-Cbl from both plasma membrane domains but process them differently. While the apically internalized TC II-Cbl is transcytosed intact to the basolateral medium, the basolaterally internalized TC II-Cbl is processed by the lysosomes involving the degradation of TC II and the liberation of Cbl to be utilized by the cell.

Apical TCII-R is Functional in Intact Intestine

Figure 5:
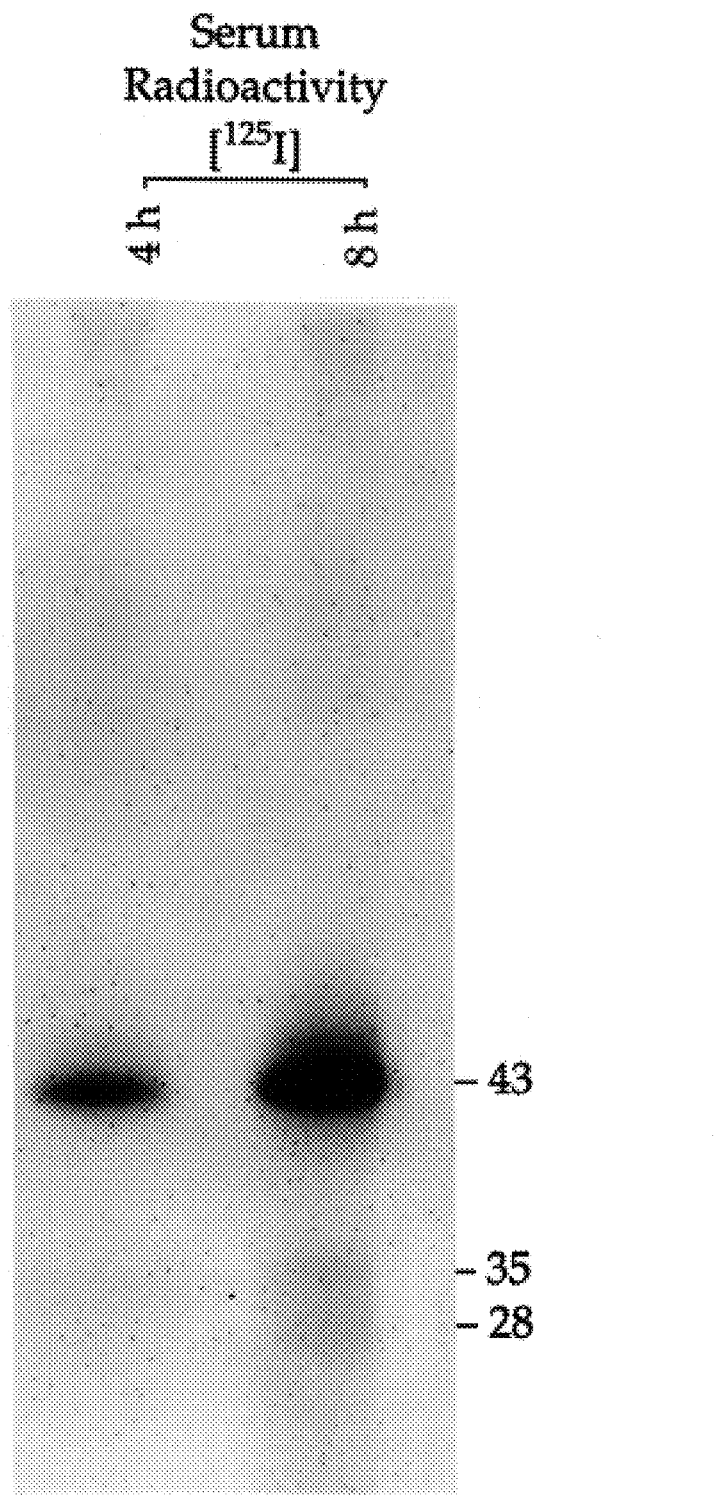
FIG. 5 is a photograph of SDS-PAGE analysis of $^{125}$I-TCII radioactivity in rat serum.

Since Caco-2 cells are derived from human colon tumors, the results obtained, the apical to basolateral transcytosis of TC II-Cbl, may be an artifact of culture and does not reflect situations in an intact intestine. In order to test whether the rat intestinal apical TCII-R is functional in the internalization of TC II-Cbl, the ligand, $^{125}$I-TC II-Cbl, was orally administered to rats. FIG. 5 is a SDS-PAGE analysis of $^{125}$I-radioactivity in rat serum- Serum was prepared from rat blood drawn following 4 hours and 8 hours of oral administration of $^{125}$I-TC II-Cbl to rats. Other details are provided in the methods section.

Following 4 hours of oral administration intact 43 kDa labeled TC II was detected [FIG. 5] in portal blood. Within 8 hours the intensity of the band had increased, but a small amount of degraded TC II of molecular mass of 35 and 28 kDa could be detected. These results show that in vivo, TCII-R expressed on the luminal side is able to mediate the transcytosis of intact TC II into systemic circulation.

Discussion

In the current studies we have used human intestinal derived epithelial Caco-2 cells to study TC II-mediated transport of Cbl. Caco-2 cells are well established cell model system and because of their high degree of differentiation they have been used extensively to study the biosynthesis and polarized delivery of functional proteins of brush border [17]. TCII-R total and specific activities [FIG. 1], like that of IFCR [7], alkaline phosphatase [18] and sucrase [17] rose as a function of differentiation of these cells. The bipolar expression and the basolateral enrichment of TCII-R noted in these cells [FIG. 3] is not an artifact of culture since isolated surface membranes from intact intestinal mucosa also exhibited this property [FIG. 2].

Recent [4] studies from our laboratory have shown that TC II-$^{57}$[Co]Cbl internalized from the basolateral side of human intestinal epithelial Caco-2 cells is processed releasing Cbl to be utilized as coenzymes by these cells. In the current studies we show that following basolateral uptake of TC II-$^{57}$[Co]Cbl, TC II is degraded by lysosomal enzymes facilitating the liberated free Cbl to be utilized by the cells. Under normal physiological conditions, the dietary Cbl present on the lumenal side bound to gastric intrinsic factor is transcytosed via IFCR in both the intact intestine [11, 19] and in Caco-2 cells [7, 20, 21] and other polarized epithelial cells [22–25]. During intrinsic factor-mediated apical to basolateral transcytosis of Cbl, intrinsic factor is degraded by leupeptin sensitive protease and Cbl is bound to transcobalamin II prior to its exit on the basolateral side [23–25]. Since all the Cbl internalized bound to IF from the apical side (luminal) of polarized epithelial cells is eventually transcytosed, these cells must obtain Cbl from endogenous sources and our current and recent [4] studies demonstrate that the basolateral TCII-R facing the circulation may facilitate such an uptake from the circulation.

The results of the current studies have also shown that the apical TCII-R expressed in Caco-cells [Table I and FIG. 4] and in the rat intestine [FIG. 5] is functional in mediating endocytosis of TC II-Cbl. The functional significance of apical endocytosis of TC II-Cbl and its eventual transcytosis by the non-lysosomal pathway in the gastrointestinal absorption of dietary/biliary Cbl is not known. It is highly unlikely that Cbl transport bound to TC II occurs physiologically bypassing the well accepted IF/IFCR pathway of Cbl transport [26] for the following two reasons: One, TC II, the ligand has never been detected in the gastrointestinal lumen despite the recent finding of relatively high levels of TC II mRNA in human pancreas [27]. However, it is not known whether TC II like IF in some species [28] is secreted from the pancreas and mediate luminal uptake of Cbl via TCII-R. Two, patients with inherited disorders [29, 30] of IF or IFCR develop Cbl deficiency, suggesting that IF/IFCR mediated Cbl transport system is the only physiologically operational intestinal uptake system for Cbl transport in man. Despite its lack of importance in the normal uptake of dietary Cbl, it is possible that apical TCII-R can mediate uptake of TC II-Cbl when presented orally, particularly in patients who malabsorb Cbl due to several inherited disorders [29, 30] or to surgical procedures such as gastrectomy and ileal resection [31]. A child who malabsorbed Cbl due to inherited TC II deficiency responded well in Schilling test [32] (which measures Cbl absorption) when the child was orally fed with Cbl complexed to TC II. Further studies are needed to test the usefulness of the apical uptake of TC II-Cbl if any, in Vitamin $B_{12}$ absorption disorders.

Based on previous [7, 20–25] and the current studies several interesting questions arise regarding the mechanism of Cbl sorting when internalized bound to IF or TC II in a polarized epithelial cell. These include a) how are these cells able to distinguish between Cbl internalized apically bound to IF or basolaterally bound to TC II to either export Cbl (transcytose) out of the cell or import it into the cell, respectively? In addition, what vesicular fusion events favor lysosomal degradation of both IF and TC II when internalized from the opposite side of these cells? and b) how do these cells process the same ligand TC II, by both the non-lysosomal and lysosomal pathways following its internalization from the apical and the basolateral domains, respectively? The cellular mechanism/s by which Caco-2 cells are able to mediate these sorting events is not known. Possible explanations for the lysosomal processing of IF or the non-lysosomal processing of TC II during apical to basolateral transcytosis of Cbl may be that it is due to a) endocytosis by two separate receptors, IFCR and TCII-R, respectively or b) due to the differences in the nature of the internalizing ligands, glycoprotein (IF) [33] vs nonglycoprotein (TC II) [34].

One observation of interest in Caco-2 cells is that endogenously synthesized [7] or exogenously derived TC II from the apical domain [FIG. 4] or exogenous TC II derived from the basolateral side whose lysosomal degradation is inhibited is secreted to the basolateral side. Even the degradation product of basolaterally derived TC II is secreted to the basolateral side. Thus, it seems that TC II, irrespective of its initial vesicular location in the cell, is targeted for basolateral secretion in these cells and perhaps in the absorptive enterocytes. The basolateral exit of TC II-Cbl in Caco-2 cells does not need TCII-R as the apical to basolateral transcytosis of TC II-Cbl occurred even when the basolateral TCII-R was inactivated with its antiserum during these experiments to ensure that the transcytosed TC II-Cbl does not re-enter the cell. The processing of TC II by two separate pathways depending on the side of internalization noted in this study may be related to the differences in the nature of the initial endocytic vesicles derived from the opposite sides of the cell or to differences in the later fusion events. Further studies are needed to define the nature of transporting vesicles and vesicular fusion events involved in the segregation of TC II taken up from the opposite side of these cells.

Figure 6:
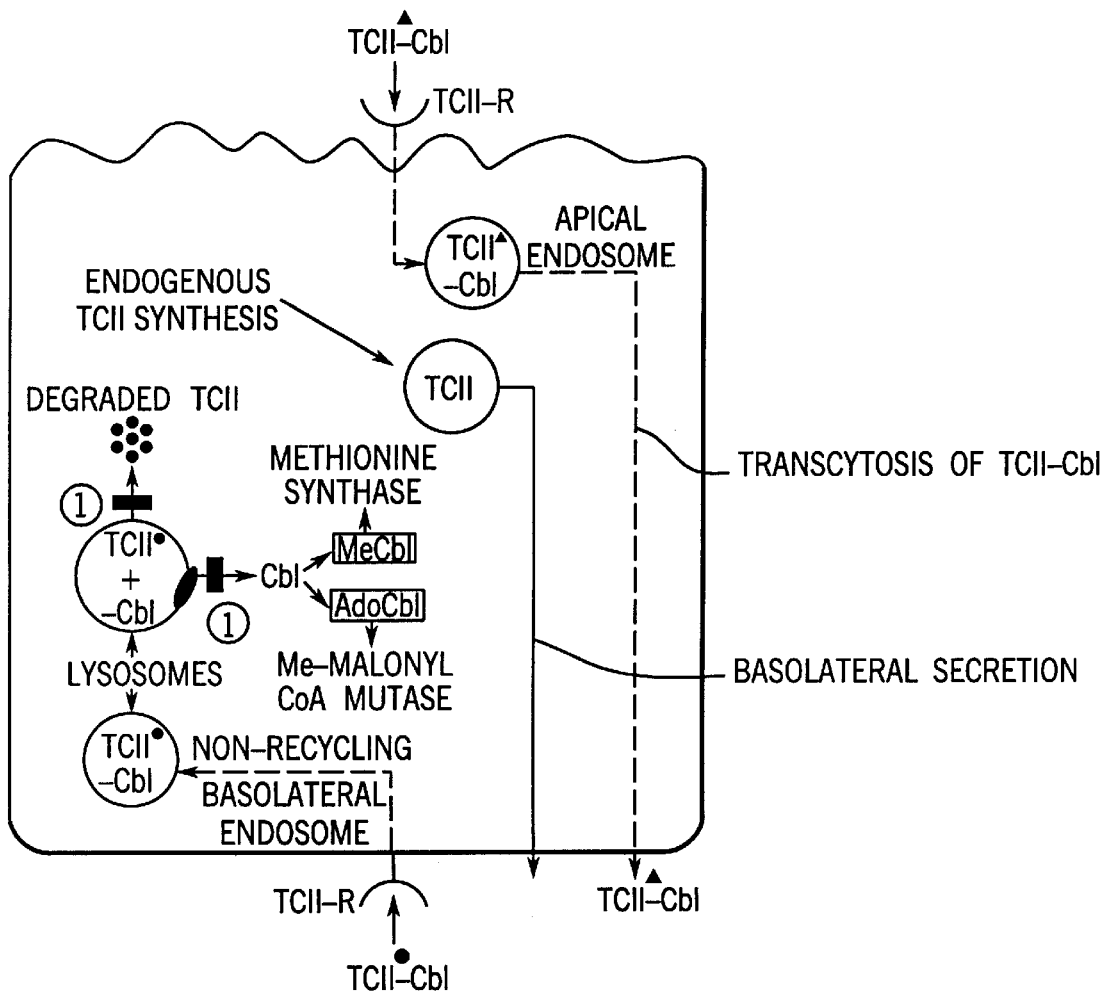
FIG. 6 is a diagram of the proposed sorting pathway of TC II and Cbl in Caco-2 cells.

Based on our previous [4] and current findings we propose a model [FIG. 6] for the TC II-mediated vectorial movement of Cbl into and out of polarized epithelial cells. FIG. 6 is the proposed sorting pathways of TC II and Cbl in Caco-2 cells-Proposed pathways are indicated by broken lines. More established pathways are indicated by full lines. TC II internalized bound to Cbl from the apical side (▲) and the basolateral side (●) is shown. The role of lysosomotropic agents, chloroquine and leupeptin on the degradation of basolaterally derived TC II and the resulting transport out of the lysosomes into the cytosol for conversion to MeCbl and AdoCbl is indicated by Block 1. The lysosomal transporter [35] which is thought to a play a role in the transfer of free Cbl from the lysosomes to the cytosol is indicated by a dark oval.

Based on this model, polarized epithelial cells, such as absorptive enterocytes derive Cbl for their intracellular utilization as Cbl coenzymes from the circulation bound to plasma TC II via TCII-R expressed in the basolateral membranes. The basolaterally derived TC II-Cbl is processed via lysosomes and free Cbl formed due to TC II degradation is transported out of the lysosomes for conversion to and utilization as Cbl coenzymes. On the other hand, apical TCII-R when presented with TC II-Cbl is able to transcytose both Cbl and TC II across the cell. Further studies are needed to test the validity of this proposal in other intestinal and renal polarized epithelial cells.

TABLE 1

Binding and internalization of TC II-[$^{57}$Co]Cbl from Caco-2 cell surface membranes
The values reported here are mean ± S.D. from 8 filters used for each experiment. Other details are provided under "Experimental Procedures."

| Side of ligand presentation | Surface-bound (5° C./ 30 min) | Internalized (37° C./1 h) [$^{57}$Co]Cbl | Intracellular (37° C./5 h) (fmol/filter) | Basolateral medium (37° C./5 h) |
|---|---|---|---|---|
| Apical | 32 ± 2 | 30 ± 3 | 5 ± 1 | 27 ± 5 |
| +Chloroquine | 32 ± 3 | 31 ± 2 | 4 ± 1 | 28 ± 4 |
| +Leupeptin | 33 ± 3 | 31 ± 2 | 3 ± 1 | 28 ± 3 |
| Basolateral | 175 ± 8 | 180 ± 5 | 178 ± 8 | 0 |
| +Chloroquine | 176 ± 7 | 172 ± 7 | 65 ± 7 | 124 ± 7 |
| +Leupeptin | 179 ± 9 | 175 ± 9 | 55 ± 5 | 120 ± 5 |

TABLE 2

Immunoprecipitation of intracellular and basolateral [$^{57}$Co]Cbl with human TC II antiserum
The results shown represent mean ± S.D. from 8 separate filters for each experiment. Other details of cell extraction and immunoprecipitation are provided under "Experimental Procedures."

| Fraction | [$^{57}$Co]Cbl immunoprecipitated | | |
|---|---|---|---|
| | Control | Chloroquine fmol/filter | Leupeptin |
| Apical ligand presentation Basolateral medium | 28 ± 2 | 27 ± 2 | 28 ± 3 |
| Basolateral ligand presentation Cellular extract | 5 ± 1 | 65 ± 5 | 55 ± 7 |
| Basolateral medium | 0 | 124 ± 5 | 128 ± 8 |

References

1. Youngdhal-Turner, P., Rosenberg, L. E. and Allen, R. H. (1978) *J. Clin. Invest.* 61:133–141.

2. Bose, S., Seetharam, S., and Seetharam, B. (1995) *J. Biol. Chem.* 270:8152–8157.

3. Bose, S., Seetharam, S., Hammond, T. G and Seetharam, B. (1995) *Biochem. J.* 310:923–929.

4. Bose, S., Komorowski, R., Seetharam, S., Gilfix, B., Rosenblatt, D. S., and Seetharam, B. (1996) *J. Biol. Chem.* 271:4195–4200.

5. Rindler, M. J and Hoops, T. C. (1994) Intracellular protein sorting in polarized epithelia. In physiology of the gastrointestinal tract. Third Edition, Edited by Leonard R. Johnson, Raven Press, New York, Chapter 46, pp. 1623–1645.

6. Rodriguez-Boulan, E., and Powell, S. K. (1992) *Ann. Rev. Cell. Biol.* 8:258–288.

7. Ramanujam, K. S., Seetharam, S., Ramasamy, M. and Seetharam, B. (1991) *Am. J. Physiol.* 260:G416–G422.

8. Lindemans, J., Kroes, A. C. M., Geel, J. V., Schoester, M., and Abels, J.(1986) *J. Exp. Cell. Res.* 184:449–460.

9. Laemmli, U. K. (1970) *Nature* 227:680–685.

10. Bose, S., Fiex, J., Seetharam, S., and Seetharam, B. (1996) *J. Biol. Chem.* 271:11718–11725.

11. Ramasamy, M., Alpers, D. H., Tiruppathi, C., and Seetharam, B.(1989) *Am. J. Physiol.* 257:G791–G797.

12. Bradford, M. M. (1976) *Analyt. Biochem.* 72:248–254.

13. Seligman, P. A. and Allen, R. H. (1978) *J. Biol. Chem.* 253:1766–1772.

14. Kessler, M., Acuto, O., Storelli, C., Murer, M., and Semenza, G. (1978) *Biochim. Biophys. Acta.* 506:136–354.

15. Molitoris, B. A., and Simon, F. R. (1985) *J. Memb. Biol.* 83:207–215.

16. Ramanujam, K. S., Seetharam, S., and Seetharam, B. (1991) *Biochem. Biophys. Res. Commun.* 179:543–550.

17. Zweibaum, A., Labruthe, M., Grasset, E., Louvard, D. (1991) Use of cultured cell lines in studies of cell differentiation and function. In Handbook of physiology, section 6. The gastrointestinal system, Volume IV. American Physiological Society, Bethesda, Md., 6:223–255.

18. Pinto, M., Robin-Leon, S., Appay, M. D., Kedinger, M., Triadou, E., Dussaulex, E., Lacroix, B., Simon-Assmann, P., Haffen, K., Fogh, J., and Zweibaum, A. (1983) *Biol. Cell.* 47:323–330.

19. Robertson, J. A., and Gallagher, N. D. (1985) *Gastroenterology* 88:908–912.

20. Dix, C. J., Hassan, I. F., Obray, H. Y., Shah, R., and Wilson, G. (1990) *Gastroenterology* 98:1272–1278.

21. Dan, N., and Cutler, D. F. (1994) *J. Biol. Chem.* 269:18849–18855.

22. Gueant, J. L., Masson, C., Schohn, H., Girr, M., Saunier, M., and Nicolas, J. P. (1992) *FEBS Lett.* 297:229–232.

23. Gordon, M. M., Howard, T., Becich, M. J., and Alpers, D. H. (1995) *Am. J. Physiol.* 268:G33–G40.

24. Ramanujam, K. S., Seetharam, S., Dahms, N., and Seetharam, B. (1991) *J. Biol. Chem.* 266:13135–13140.

25. Ramanujam, K. S., Seetharam, S., and Seetharam, B. (1992). *Biochem. Biophys. Res. Commun.* 182:439–446.

26. Seetharam, B. (1994) Gastrointestinal absorption and transport of cobalamin (Vitamin $B_{12}$). In Physiology of the gastrointestinal tract. Ed. by Leonard R. Johnson. Raven Press, New York, Third Edition, Chapter 61, pp. 1997–2026.

27. Li, N., Seetharam, S., Rosenblatt, D. S and Seetharam, B. (1994) *Biochem. J.* 310:585–590.

28. Batt, R. M., and Horadagoda, N. U. (1989) *Am. J. Physiol.* 257:G9344–G9349.

29. Cooper, B. A., and Rosenblatt, D. S. (1987) *Ann. Rev. Nutr.* 7:291–296.

30. Fenton, W. A. and Rosenberg, L. E. (1989) Inherited disorders of cobalamin transport and metabolism. In Metabolic basis of inherited disease, 2nd ed. Scriver, C. R., Beaudet, A. L., Sly, W. S., Valley, D., eds.: McGraw Hill Information Service Company.

31. Seetharam, B., and Alpers, D. H. (1982) *Ann. Rev. Nutr.* 2:343–369.

32. Barshop, B. A., Wolf, J., Nyham, W. L., Alice, Y. Prodanos, C., Jones, G., Sweetman, L., Leslie, J., Holm, J., Green, R., Jacobsen, D. W., Cooper, B. A., Rosenblatt, D. S. (1990). *Am. J. Med. Genetics* 35:222–228.

33. Allen, R. H., and Mehlman, C. S. (1973). *J. Biol. Chem.* 248:3600–3609.

34. Allen, R. H., and Majerus, P. W. (1972). *J. Biol. Chem.* 247:7709–7717.

35. Idriss, J. M., and Jonas, A. J. (1991) *J. Biol. Chem.* 266:9538–9441.

We claim:

1. A method of treating a vitamin $B_{12}$ deficient patient comprising the steps of orally delivering an effective amount of vitamin $B_{12}$ via a transcobalamin II-cobalamin complex to a patient, wherein the patient has a deficiency of intrinsic factor receptor or intrinsic factor.

* * * * *